(12) United States Patent
Sokolov et al.

(10) Patent No.: US 8,246,249 B2
(45) Date of Patent: Aug. 21, 2012

(54) APPARATUS AND METHOD FOR RECORDING RADIATION IMAGE DATA OF AN OBJECT

(75) Inventors: Skiff Sokolov, Lidingö (SE); Christer Ullberg, Sollentuna (SE); Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 219 days.

(21) Appl. No.: 12/733,696

(22) PCT Filed: Oct. 7, 2008

(86) PCT No.: PCT/SE2008/051141
§ 371 (c)(1),
(2), (4) Date: Mar. 16, 2010

(87) PCT Pub. No.: WO2009/048419
PCT Pub. Date: Apr. 16, 2009

(65) Prior Publication Data
US 2010/0215145 A1 Aug. 26, 2010

(30) Foreign Application Priority Data
Oct. 9, 2007 (SE) ........................................ 0702258

(51) Int. Cl.
*H05G 1/02* (2006.01)
(52) U.S. Cl. .......................................... 378/197; 378/25
(58) Field of Classification Search .................... 378/21, 378/25, 27, 37–40, 98.8, 146, 156–158, 193–198
See application file for complete search history.

(56) References Cited

U.S. PATENT DOCUMENTS

| 2,000,497 | A | * | 5/1935 | Pohl ................................ 378/25 |
| 4,541,293 | A | | 9/1985 | Caugant |
| 5,038,371 | A | | 8/1991 | Janssen |
| 6,118,125 | A | | 9/2000 | Carlson |
| 6,196,715 | B1 | | 3/2001 | Nambu |
| 6,337,482 | B1 | | 1/2002 | Francke |
| 6,373,065 | B1 | | 4/2002 | Francke |

(Continued)

FOREIGN PATENT DOCUMENTS
FR 2888488 1/2007
(Continued)

OTHER PUBLICATIONS

Graeme P. Penney, et al. "A Comparison of Similarity Measures for Use in 2-D-3-D Medical Image Registration." IEEE Transactions on Medical Imaging, vol. 17, No. 4, Aug. 1998.

*Primary Examiner* — Courtney Thomas
(74) *Attorney, Agent, or Firm* — Harness, Dickey & Pierce, P.L.C.

(57) ABSTRACT

An apparatus for recording radiation image data of an object comprises a radiation source arrangement (3) provided for emitting radiation; an object holder (5) arranged in the radiation path of the emitted radiation and provided for housing the object during the recordation of the radiation image data; a detector arrangement (6) for detecting radiation which has interacted with the object; a support structure (2), to which the radiation source and detector arrangements are secured; and a scanning device (1) provided for moving either one of the support structure or the object holder with respect to the other one of the support structure or the object holder in a conical pendulum movement while the detector arrangement is provided for detecting radiation which has interacted with the object.

19 Claims, 1 Drawing Sheet

U.S. PATENT DOCUMENTS

| | | |
|---|---|---|
| 6,414,317 B1 | 7/2002 | Francke |
| 6,435,714 B1 | 8/2002 | Bruder |
| 6,476,397 B1 | 11/2002 | Francke |
| 6,477,223 B1 | 11/2002 | Francke |
| 6,518,578 B1 | 2/2003 | Francke |
| 6,522,722 B1 | 2/2003 | Francke |
| 6,546,070 B1 | 4/2003 | Francke |
| 6,600,804 B2 | 7/2003 | Francke |
| 6,784,436 B2 | 8/2004 | Francke |
| 6,856,669 B2 | 2/2005 | Francke |
| 6,873,682 B2 | 3/2005 | Francke |
| 6,940,942 B2 | 9/2005 | Ullberg |
| 7,016,458 B2 | 3/2006 | Francke |
| 7,020,237 B2 | 3/2006 | Francke |
| 7,027,561 B2 * | 4/2006 | Francke et al. ............... 378/146 |
| 7,099,436 B2 | 8/2006 | Francke |
| 7,123,682 B2 | 10/2006 | Kotian |
| 7,127,029 B2 | 10/2006 | Francke |
| 7,164,748 B2 | 1/2007 | Francke |
| 7,180,977 B2 | 2/2007 | Francke |
| 7,403,591 B2 | 7/2008 | Wink |
| 2001/0054695 A1 | 12/2001 | Lienard |
| 2005/0047544 A1 | 3/2005 | Fu |
| 2005/0135557 A1 | 6/2005 | Hermann Claus |
| 2005/0219243 A1 | 10/2005 | Kidera |
| 2005/0234327 A1 | 10/2005 | Saracen |
| 2007/0253528 A1 | 11/2007 | Ning |
| 2007/0268999 A1 | 11/2007 | Ullberg |
| 2009/0074130 A1 | 3/2009 | Francke |

FOREIGN PATENT DOCUMENTS

| | | |
|---|---|---|
| JP | 9-212633 | 8/1997 |
| JP | 2005-92575 | 4/2005 |
| WO | WO 98/24368 | 6/1998 |
| WO | WO 2006/018768 | 2/2006 |

* cited by examiner

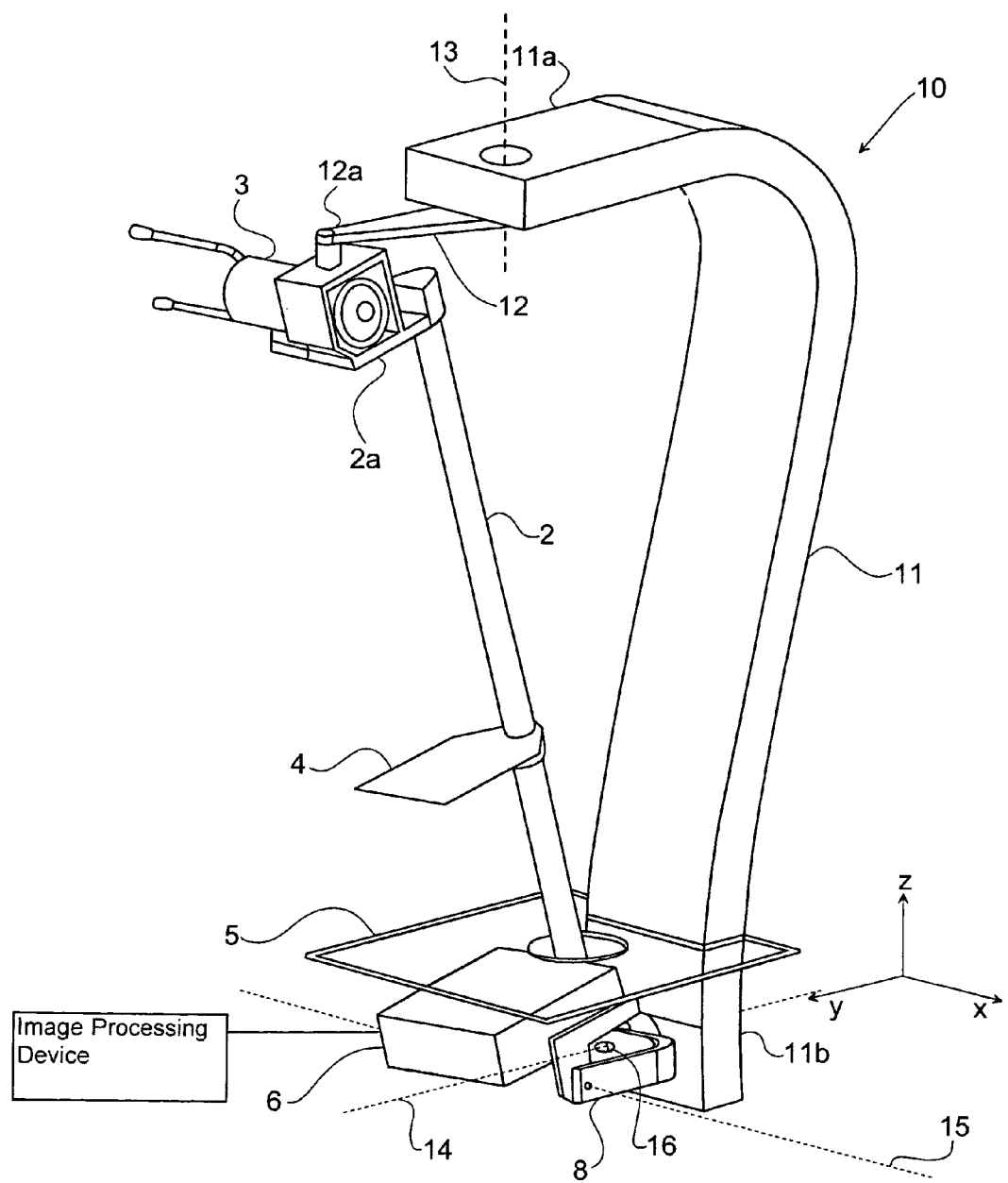

APPARATUS AND METHOD FOR RECORDING RADIATION IMAGE DATA OF AN OBJECT

FIELD OF THE INVENTION

The invention relates generally to radiation examination, and particularly to an apparatus and a method for recording radiation image data of an object.

BACKGROUND OF THE INVENTION AND RELATED ART

In X-ray medical diagnostics one or more images of a part of a patient such as an abdominal organ thereof, which is to be examined, is created. In tomosynthesis imaging a plurality of images is acquired at different angles. By shifting and adding the plurality of images, it is possible to reconstruct any plane in the patient being examined.

Further, various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. To use such a detector in tomosynthesis, wherein a plurality of images has to be acquired at different angles would be very time consuming.

SUMMARY OF THE INVENTION

An object of the invention is to provide an apparatus and a method, respectively, for recording radiation image data of an object at high speed simultaneously as data from many angles are recorded.

A further object of the invention is to provide such apparatus and method, which are uncomplicated and can record radiation image data for producing a high-quality three-dimensional radiation image such as three-dimensional tomosynthesis image and a high-quality two-dimensional radiation image such as a two-dimensional projection image with high spatial resolution, signal-to-noise ratio, dynamic range, and image contrast, while the imaging object is exposed to a minimum of radiation.

A still further object of the invention is to provide such apparatus and method, which are capable of instantaneously recording, by means of multiple one-dimensional detectors, at least multiple one-dimensional images of the object, and, by means of scanning, at least multiple two-dimensional images of the object, where each of the one-dimensional images of the object is recorded at a different angle.

A yet further object of the invention is to provide such method and apparatus, which are reliable, accurate, and inexpensive.

These objects, among others, are attained by apparatuses and methods as claimed in the appended claims.

According to a first aspect of the invention an apparatus for recording radiation image data of an object is provided. The apparatus comprises a radiation source arrangement, which emits radiation, an object holder arranged in the radiation path of the emitted radiation, which houses the object during the recordation of the radiation image data, a detector arrangement, which detects radiation which has interacted with the object, a support structure, to which the radiation source and detector arrangements are secured, and a scanning device, which moves either one of the support structure and the object holder with respect to the other one of the support structure and the object holder in a conical pendulum movement while the detector arrangement detects radiation, which has interacted with the object. Hereby the radiation image data of the object is recorded.

In one embodiment the scanning device moves either one of the support structure or the object holder in an elliptic conical pendulum movement while the detector arrangement detects radiation, which has interacted with the object.

In another embodiment the scanning device moves either one of the support structure or the object holder in conical pendulum movements with varying cone radii while the detector arrangement detects radiation, which has interacted with the object.

Preferably, the scanning device moves either one of the support structure or the object holder in a conical pendulum movement with a center of rotation lying downstream of the detector arrangement or upstream of the radiation source arrangement while the detector arrangement detects radiation, which has interacted with the object. Provided that the apparatus is oriented vertically with, from top to bottom, the radiation source arrangement, the object holder, and the detector arrangement, the center of rotation lies preferably below the detector arrangement or above the radiation source arrangement.

The present invention provides for recordation of radiation image data of an object at high speed simultaneously as data from many angles are recorded. From the radiation image data any of a three-dimensional radiation image, a two-dimensional radiation image, a two-dimensional radiation projection image, a three-dimensional tomosynthesis image, or a two-dimensional tomosynthesis image, of the object can be created.

According to a second aspect of the invention a method for recording radiation image data of an object is provided. According to the method radiation is emitted by a radiation source, an object is arranged in the radiation path of the emitted radiation during the recordation of the radiation image data, and either the radiation source and detector arrangements or the object are/is moving with respect to the other one of the radiation source and detector arrangements or the object in a conical pendulum movement while radiation, which has interacted with the object, is detected, thereby recording the radiation image data of the object.

The present invention is applicable in several technical fields such as medical examinations, baggage checking, and material testing. In particular, the invention is applicable to all kind of abdominal organ examinations.

Further characteristics of the invention and advantages thereof, will be evident from the detailed description of embodiments of the present invention given hereinafter and the accompanying FIG. 1, which is given by way of illustration only and thus, is not limitative of the present invention.

BRIEF DESCRIPTION OF THE DRAWING

FIG. 1 illustrates schematically, in a perspective view, an apparatus for recording radiation image data of an object according to an embodiment of the present invention.

DESCRIPTION OF EMBODIMENTS

The apparatus of FIG. 1 comprises a support structure 2, to which a radiation source arrangement 3, a collimator/filter arrangement 4, and a detector arrangement 6 are secured, preferably rigidly secured.

The radiation source arrangement 3 is provided for emitting radiation and comprises preferably a divergent X-ray tube, which produces X-rays centered around an axis of symmetry.

The detector arrangement 6 is provided for detecting radiation which has interacted with the object. Typically, the detector arrangement 6 comprises one or several stacks of one-dimensional detectors.

In one embodiment the detector arrangement 6 comprises a stack of line detectors, each being directed towards the radiation source arrangement 2 to allow a ray bundle of the radiation that propagates in a respective one of a plurality of different angles to enter the line detector, and each one of the line detectors is provided to record line images of radiation as transmitted through the object in different angles.

Alternatively, or additionally, the detector arrangement 6 may comprise a stack of line detectors, each of which being a gaseous-based ionization detector, wherein electrons freed as a result of ionization by the radiation are accelerated in a direction essentially perpendicular to the direction of the radiation.

Detector arrangements and detectors of the above kind are further detailed in the following U.S. Patents assigned to XCounter AB of Sweden, the contents of which are hereby incorporated by reference: U.S. Pat. Nos. 6,118,125; 6,337,482; 6,373,065; 6,414,317; 6,476,397; 6,477,223; 6,518,578; 6,522,722; 6,546,070; 6,600,804; 6,784,436; 6,856,669; 6,873,682; 6,940,942; 7,016,458; 7,020,237; 7,099,436; 7,127,029; 7,164,748; and 7,180,977.

Yet alternatively, the detector arrangement 6 may comprise a one-dimensional or two-dimensional scintillator-based detector, a PIN-diode array, a TFT array, a CMOS pixel detector, a CCD array, a liquid-based detector, or a solid-state detector.

The collimator/filter arrangement 4, which is optional, may comprise a thin foil of e.g. tungsten with narrow radiation transparent slits etched away, the number of which corresponds to the number of line detectors of the detector arrangement 6. The slits are aligned with the line detectors of the detector arrangement 6 so that X-rays passing through the slits of the collimator/filter arrangement 4 will reach the line detectors of the detector arrangement 6 as respective ray bundles. The collimator/filter arrangement 4 prevents radiation, which is not directed directly towards the line detectors of the detector arrangement 6, from impinging on an object to be examined, thereby reducing the radiation dose to the object. This is advantageous in all applications where the object is a human or an animal, or parts thereof.

Furthermore, the collimator/filter arrangement 4 may comprise thin foils to filtrate the radiation.

In one embodiment the collimator/filter arrangement 4 is capable of operating in two different operation modes, one at a time, wherein the operation modes have different filter characteristics. In such instance the collimator/filter arrangement 4 can be provided for altering operation mode subsequent to at least every second one of a plurality of detections made to thereby provide for dual energy detection.

Alternatively, the collimator/filter arrangement 4 comprises an array of filter sections wherein the filter sections have different filter characteristics and different filter sections cover different ones of the narrow radiation transparent slits. Also in this case dual energy detection is enabled.

The above embodiments are further detailed in the following U.S. Patent assigned to XCounter AB of Sweden, the contents of which are hereby incorporated by reference: U.S. Pat. No. 7,027,561.

The apparatus of FIG. 1 further comprises a scanning device 10 provided for moving the support structure 2 (and thus the radiation source arrangement 3, the optional collimator/filter arrangement 4, and the detector arrangement 6) in a conical pendulum movement while the detector arrangement 6 detects, preferably repeatedly detects, radiation, which has interacted with the object, to thereby record the radiation image data of the object. The conical pendulum movement is typically performed around a vertical axis z.

Hereby, radiation image data of the object can be recorded at a large number of different angles for the incident radiation. Such large angle radiation image data provides for a high spatial resolution in the z direction, that is, in a direction essentially parallel with the incident radiation. Furthermore, the conical pendulum movement, which is similar to a precession movement, provides for continuous scanning along a given path, preferably in one direction only along the path. Measurements at high speeds are thus enabled.

The scanning device 10 comprises a support frame 11, an arm 12 rotatably attached to an upper portion 11a of the support frame 11 and a member 8 pivotably attached to a lower portion 11b of the support frame 11.

The arm 12 is capable of being rotated around a vertical axis 13, which is parallel with the z axis, by means of e.g. a motor (not illustrated). An upper end portion 2a of the support structure 2 is suspending from an outer end portion 12a of the arm 12 such that the upper end portion 2a of the support structure 2 can be moved around a circle in the horizontal plane (xy plane) as the arm 10 rotates without the support structure 2 being rotated.

The member 8 is capable of being pivoted around an axis 14, which is parallel with the y axis, and is pivotably attached to the support structure 2 such that the support structure 2 is capable of being pivoted around an axis 15, which is parallel with the x axis.

An object holder 5 for housing the object during the recordation of the radiation image data is arranged in the radiation path of the emitted radiation from the radiation source arrangement 3. The object holder 5 is rigidly attached to the support frame 11 between the attachments of the optional collimator/filter arrangement 4 and the member 8 and to this end the object holder 5 comprises an opening through which the support structure 2 may extend. Radiation transmitted through the object, which is kept still, is thus typically detected by the detector arrangement 6.

The scanning device 10 moves the support structure 2 in a conical pendulum movement with a center of rotation 16 lying downstream of the detector arrangement 6, that is, below the detector arrangement 6. It shall be appreciated that the center of rotation may instead lie upstream of the radiation source arrangement 3, that is, above the radiation source arrangement 3, in level with the detector arrangement 6 or the radiation source arrangement 3, or between the detector arrangement 6 and the radiation source arrangement 3 but outside the object during recordation of the radiation image data. The last fact is important in order to create three-dimensional images of the object from the recordation data. A rotation center far from the object is preferred since by such measures larger radiation angles for the radiation through the object will be obtained, which means a better spatial resolution in the images produced from the recorded data, in particular in directions essentially parallel with a main direction of the radiation, i.e. the vertical direction.

In one embodiment the scanning device 10 is provided for moving the support structure 2 in an elliptic conical pendulum movement while the detector arrangement 6 detects radiation, which has interacted with the object.

In another embodiment the scanning device 10 is provided for moving the support structure 2 in conical pendulum movements with a continuously varying cone radii while the detector arrangement 6 detects radiation, which has interacted with the object.

The above movements can be achieved by automatically moving the arm 12 linearly in a radial direction by a linear moving unit while being rotated around the vertical axis 13. Such linear movement can be realized in a plurality of manners readily available to a person skilled in the art.

It shall be appreciated that the enclosed path which the radiation source arrangement 3 (or other part of the apparatus) undergoes during the conical pendulum movement may have other shapes than the above described circular, elliptical, and spiral shapes. Generally, the enclosed path of a base of the cone formed by the pendulum movement may have any shape.

However, recording measurements at different cone radii may be preferred since such measurements provide recordation of the radiation image data with radiation at more different angles. Hereby a better spatial resolution is obtainable, in particular in directions essentially parallel with the main direction of the radiation.

Further, the conical pendulum movement may be performed around a non-vertical axis.

Generally, the term conical pendulum movement encompasses any pendulum movement along the lateral surface of a cone, which may have a base of any arbitrary shape and an axis running from the apex of the cone to the center of the base (as suitably defined) of any arbitrary orientation.

Yet further, the scanning device 10 may move the support structure 2 (and thus the radiation source arrangement 3, the optional collimator/filter arrangement 4, and the detector arrangement 6) vertically while performing the conical pendulum movement.

Still further, the scanning device 10 may rotate the support structure 2 e.g. in a plane orthogonal to the longitudinal direction of the support structure during the conical pendulum movement. Alternatively, only some of the parts (the radiation source arrangement 3, the optional collimator/filter arrangement 4, and the detector arrangement 6), such as e.g. the detector arrangement 6 is rotated during the conical pendulum movement.

The scanning device 10 moves typically the support structure 2 in the conical pendulum movement essentially one full revolution, even though some applications require longer or shorter scanning movements.

The detector arrangement 6 detects radiation, which has interacted with the object, typically at least a plurality of times, preferably at least 10 times, more preferably at least 100 times, and most preferably at least 1000 times, for each revolution of the conical pendulum movement.

It shall be appreciated that while the embodiment of FIG. 1 has been described as being arranged so that the scanning device 10, during scanning, moves the support structure 2 (and thus the radiation source arrangement 3, the optional collimator/filter arrangement 4, and the detector arrangement 6) in a conical pendulum movement while the object holder 5 (and thus the object) is kept still, the invention encompasses also the opposite alternative, that is, the scanning device 10 moves the object holder 5 (and thus the object) in a conical pendulum movement while the support structure 2 (and thus the radiation source arrangement 3, the optional collimator/filter arrangement 4, and the detector arrangement 6) is kept still.

Further, the apparatus of the invention may comprise an image processing device provided for creating any of a three-dimensional radiation image, a two-dimensional radiation image, a two-dimensional radiation projection image, a three-dimensional tomosynthesis image, or a two-dimensional tomosynthesis image, of the object from the recorded radiation image data, and a display device (not explicitly illustrated) provided for displaying the created image. Such apparatuses and devices are further detailed in our pending U.S. patent application Ser. No. 11/447,901 filed on Jun. 6, 2006 and Swedish patent application No. 0702061-3 filed on Sep. 17, 2007, as well as in U.S. Pat. No. 6,196,715 B1; US 2005/0135557 A1; US 2005/0047544 A1; US 2005/0219243; JP9212633; JP 2005 092575 A; and G.P. Penney et al., A Comparison of Similarity Measures for Use in 2-D-3-D Medical Image Registration, IEEE Transactions on Medical Imaging, Vol. 17, No. 4, August 1998, the contents of which being hereby incorporated by reference.

The invention claimed is:

1. An apparatus for recording radiation image data of an object comprising
a radiation source arrangement provided for emitting radiation;
an object holder arranged in the radiation path of said emitted radiation and provided for housing the object during the recordation of the radiation image data;
a detector arrangement for detecting radiation, which has interacted with said object; and
a support structure, to which said radiation source and detector arrangements are secured, comprising:
a scanning device provided for moving either one of said support structure or said object holder with respect to the other one of said support structure or said object holder in a conical pendulum movement while said detector arrangement is provided for detecting radiation, which has interacted with said object, to thereby record said radiation image data of the object, said conical pendulum movement having a center of rotation lying outside the object.

2. The apparatus of claim 1 wherein said scanning device is provided for moving either one of said support structure or said object holder around a vertical axis.

3. The apparatus of claim 1 wherein said scanning device is provided for moving either one of said support structure or said object holder in an elliptic conical pendulum movement while said detector arrangement is provided for detecting radiation, which has interacted with said object.

4. The apparatus of claim 1 wherein said scanning device is provided for moving either one of said support structure or said object holder in conical pendulum movements with varying cone radii while said detector arrangement is provided for detecting radiation, which has interacted with said object.

5. The apparatus of claim 1 wherein said center of rotation lies downstream of said detector arrangement or upstream of said radiation source arrangement.

6. The apparatus of claim 1 wherein said scanning device is provided for moving either one of said support structure or said object holder in said conical pendulum movement one full revolution.

7. The apparatus of claim 1 wherein said detector arrangement is, during said conical pendulum movement, provided for repeatedly detecting radiation which has interacted with said object.

8. The apparatus of claim 1 wherein said detector arrangement is provided for detecting radiation, which has interacted with said object, at least a plurality of times, during each revolution of the conical pendulum movement.

9. The apparatus of claim 1 wherein
said detector arrangement comprises a stack of line detectors, each being directed towards the radiation source arrangement to allow a ray bundle of the radiation that propagates in a respective one of a plurality of different angles to enter the line detector; and
each one of said line detectors is provided to record line images of radiation as transmitted through the object in different angles.

10. The apparatus of claim 1 wherein said detector arrangement comprises a stack of line detectors, wherein the line detectors are each a gaseous-based ionization detector, wherein electrons freed as a result of ionization by the radiation are accelerated in a direction perpendicular to the direction of the radiation.

11. The apparatus of claim 1 wherein said detector arrangement comprises a scintillator-based detector, a PIN-diode array, a TFT array, a ,CMOS pixel detector, a CCD array, a liquid-based detector, or a solid-state detector.

12. The apparatus of claim 1 comprising an image processing device provided for creating any of a three-dimensional radiation or tomosynthesis image of the object from the recorded radiation image data.

13. A method for recording radiation image data of an object comprising
emitting radiation by a radiation source arrangement;
arranging an object in the radiation path of said emitted radiation during the recordation of the radiation image data; and
detecting radiation, which has interacted with said object, by a detector arrangement by:
moving either said radiation source and detector arrangements or said object with respect to the other one of said radiation source and detector arrangements or said object in a conical pendulum movement while detecting radiation, which has interacted with said object, thereby recording said radiation image data of the object, said conical pendulum movement having a center of rotation lying outside the object.

14. The method of claim 13 wherein either said radiation source and detector arrangements or said object holder are/is moved in an elliptic conical pendulum movement while radiation, which has interacted with said object, is detected.

15. The method of claim 13 wherein either said radiation source and detector arrangements or said object holder are/is moved in conical pendulum movements with varying cone radii while radiation, which has interacted with said object, is detected.

16. The method of claim 13 wherein either said radiation source and detector arrangements or said object holder are/is moved in an elliptic conical pendulum movement while radiation, which has interacted with said object, is detected.

17. The method of claims 13 wherein said center of rotation lies downstream of said detector arrangement or upstream of said radiation source arrangement.

18. The method of claim 13 wherein either said radiation source and detector arrangements or said object holder are/is moved in a conical pendulum movement one full revolution while radiation, which has interacted with said object, is detected.

19. The method of claim 13 comprising creating any of a three-dimensional radiation or tomosynthesis image of the object from the recorded radiation image data by means of digital image processing.

* * * * *